United States Patent

Yoshioka et al.

[11] 4,092,474
[45] May 30, 1978

[54] CEPHALOSPORINS HAVING A METALOXY GROUP IN 3-SUBSTITUENT

[75] Inventors: Mitsuru Yoshioka, Toyonaka; Yuji Sendo, Ikeda; Masayuki Murakami, Itami, all of Japan

[73] Assignee: Shionogi & Co., Ltd., Osaka, Japan

[21] Appl. No.: 637,477

[22] Filed: Dec. 3, 1975

[30] Foreign Application Priority Data

Dec. 6, 1974 Japan .............................. 49-140775

[51] Int. Cl.² .................. C07D 501/16; C07D 501/34; C07D 501/28; A61K 31/545

[52] U.S. Cl. .......................................... 544/17; 544/4; 544/16; 544/21; 544/22; 544/29; 424/246

[58] Field of Search .................. 260/243 C; 424/246; 544/16, 17, 21, 22, 29, 4

[56] References Cited

U.S. PATENT DOCUMENTS

| | | | |
|---|---|---|---|
| 3,351,596 | 11/1967 | Chamberlin | 260/243 C |
| 3,947,413 | 3/1976 | Christensen et al. | 260/243 C |
| 3,983,113 | 9/1976 | Beeby | 260/240 R |
| 4,012,380 | 3/1977 | Spry | 260/243 C |

*Primary Examiner*—Donald G. Daus
*Assistant Examiner*—Diana G. Rivers
*Attorney, Agent, or Firm*—Wenderoth, Lind & Ponack

[57] ABSTRACT

Antibacterial cephalosporins of the formula

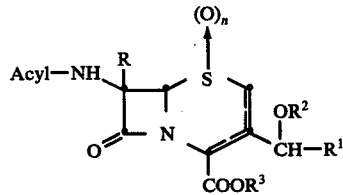

wherein Acyl is an acyl group; R is a hydrogen or methoxy, $R^1$ is a hydrocarbyl group containing 1 to 8 carbon atoms; $R^2$ is a hydrogen, alkali metal, alkaline earth metal, halo-alkaline earth metal group or acyl group containing 1 to 12 carbon atoms; $R^3$ is a hydrogen, pharmaceutically acceptable cation, or ester residue; or when $R^2$ and $R^3$ are both hydrogens, they can be combined to form a lactone ring; the broken line shows a double bond at position 2 or 3; and $n$ is zero or one, and processes for preparing them by the reaction of the compound shown by above formula in which $R^1$ and $R^2$ combined to show a bond, with a Grignard type or organometallic reagent to introduce $R^1$, followed by acylation, oxidation, reduction, double bond migration, or other reactions.

11 Claims, No Drawings

CEPHALOSPORINS HAVING A METALOXY GROUP IN 3-SUBSTITUENT

This invention relates to antibacterial cephalosporins of the general formula

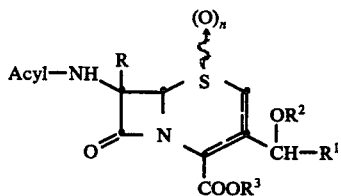

wherein Acyl is an acyl group; R is a hydrogen or methoxy; $R^1$ is a hydrocarbyl group containing 1 to 8 carbon atoms; $R^2$ is a hydrogen, alkali metal, alkaline earth metal, halo-alkaline earth metal group or acyl group containing 1 to 12 carbon atoms; $R^3$ is a hydrogen, pharmaceutically acceptable cation, or ester residue; or when $R^2$ and $R^3$ are both hydrogens, they can be combined to form a lactone ring; the broken line shows a double bond at position 2 or 3; and $n$ is zero or one, and processes for preparing them.

In above definitions, the hydrocarbyl group containing 1 to 8 carbon atoms shown by $R^1$ can be alkyl, cycloalkyl, aralkyl, or aryl containing 1 to 8 carbon atoms, capable of forming organometalic reagents, and optionally substituted by an inert group e.g. alkyl, alkoxy, alkylamino, or alkylthio containing 1 to 5 carbon atoms. The alkali metal of $R^2$ can be lithium, sodium, and potassium, and the alkaline earth metal can be magnesium, cadminium, and zinc. The halo-alkaline earth metal group of $R^2$ can be chloromagnesio, bromomagnesio, iodomagnesio, bromozinc, bromocadmium, and the acyl group of $R^2$ can be alkanoyl, aralkanoyl, aroyl, sulfonyl, or carbonic acyl containing 1 to 12 carbon atoms. The acyl group of Acyl is conventional acyl groups in the field of penicillin and cephalosporin chemistry. Representative acyl groups can be alkanoyl (e.g. formyl, acetyl, butyryl, pivaloyl, cyclopentylcarbonyl, cyclohexyl carbonyl, cyclohexylacetyl, cycloheptylacetyl, dihydrophenylacetyl, crotonyl, methoxyacetyl, methylthioacetyl, isopropenylthioacetyl, phenoxyacetyl, phenylthioacetyl, benzyloxyacetyl), aroyl (e.g. benzoyl, xyloyl, naphthoyl, phthaloyl, tetrahydronaphthoyl, nicotinoyl, pyrazinoyl, 3-methyl-5-phenylisoxazol-4-carbonyl), aralkanoyl (e.g. phenylacetyl, phenylpropionyl, tolylacetyl, naphthylacetyl, tetrahydronaphthylacetyl, tetrazolylacetyl, thienylacetyl, thienylpropionyl, furylacetyl, pyrimidylacetyl, pyrylacetyl, isoxazolylacetyl, benzoisothiazolylacetyl, benzoxazolylacetyl), carbonic acyl (e.g. cyclohexyloxycarbonyl, cycloheptyloxycarbonyl, benzyloxycarbonyl, phenoxycarbonyl, naphthoxycarbonyl, pyridylmethoxycarbonyl, 2,2,2-trichloroethoxycarbonyl, cyclopropylethoxycarbonyl), phosphoric acyl, sulfuric acyl, sulfenyl acyl (e.g. phenylsulfenyl, o-nitrophenylsulfenyl, benzylsulfenyl), and other acyl groups conventional in the art.

More specific acyl groups for Acyl in the formula I include a member selected from the group consisting of the following groups:

1. alkanoyl containing 1 to 5 carbon atoms;
2. haloalkanoyl containing 2 to 5 carbon atoms;
3. acyl groups of following formula:

Ar—CQQ'—CO— in which Q and Q' each is a hydrogen or a methyl; and Ar is a phenyl, dihydrophenyl, or monocyclic hetrocyclic aromatic group containing 1 to 4 hetero atoms selected from nitrogen, oxygen, and/or sulfur atoms, and optionally substituted by an inert group e.g. an alkyl or alkoxy containing 1 to 3 carbon atoms;
4. acyl groups of the following formula Ar—G—CQQ'—CO— in which G is an oxygen or sulfur; Ar, Q, and Q' are as defined above;
5. sydnon-alkanoyl containing 3 to 5 carbon atoms;
6. acyl groups of the following formula

L—O—CO— in which L is an easily removable optionally substituted hydrocarbon group containing 1 to 8 carbon atoms;
7. acyl groups of the following formula Ar—CHT—CO— in which Ar is as defined above; and T is (i) amino, ammonium, amino substituted by such conventional amino-protecting groups as benzyloxycarbonyl, alkoxycarbonyl containing 1 to 4 carbon atoms, cyclopentyloxycarbonyl, cyclohexyloxycarbonyl, benzhydryloxycarbonyl, cyclopropylmethoxycarbonyl, methanesulfonylethoxycarbonyl, triphenylmethyl, 2,2,2-trichloroethoxycarbonyl, guanidylcarbamoyl, optionally substituted ureido carbonyl, alkanoyl containing 1 to 5 carbon atoms, pyronecarbonyl, thiopyridonecarbonyl homo- or hetero-cyclic mono-cyclic aromatic acyl optionally substituted by hydroxy, lower alkanoyloxy containing from 1 to 3 carbon atoms, halogen, trifluoromethyl, or alkyl containing 1 to 3 carbon atoms, aminoalkyl containing 1 to 3 carbon atoms, or hydroxyalkyl containing 1 to 3 carbon atoms, or amino protected in the forms of phthalimido or enamines derived from acetoacetates, acetylacetone, or acetoacetamide (ii) hydroxy or acyloxy containing from 1 to 7 carbon atoms, (iii) carboxy or alkoxycarbonyl containing from 2 to 7 carbon atoms, indanyloxycarbonyl, phenoxycarbonyl, or (iv) azido, cyano, carbamoyl, alkoxysulfonyl, sulfo, aminosulfo, or alkoxysulfonyl; or HT combined represent a hydroxyimino or alkoxyimino;

In the above definitions, representative Ar groups are exemplified by furyl, thienyl, pyrryl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, phenyl, pyridyl, pyrimidyl, pyrazinyl, pyridazinyl, triazinyl, or dihydrophenyl, each being optionally substituted by a halogen, alkyl containing 1 to 3 carbon atoms, hydroxy, aminomethyl or alkoxy containing 1 to 3 carbon atoms.

The ester residue shown by $R^3$ can be those forming conventional alkyl esters (e.g. methyl, ethyl, tertiary butyl, cyclohexyl, propenyl, methoxymethyl, ethoxymethyl, methylthioethyl, phenoxymethyl, phenylthiomethyl, toluoylmethyl, chloromethyl, bromomethyl, trichloroethyl, cyanomethyl, nitrophenylthiomethyl, chlorophenoxymethyl, chlorophenacyl, nitrophenacyl, dimethylaminoethyl, diethylaminoethyl esters), aryl ester (e.g. phenyl, xylyl, naphthyl, pentachlorophenyl, trichlorophenyl, p-methanesulfonylphenyl, p-phenylazophenyl, dinitrophenyl, pyridyl, quinolyl-esters), aralkyl ester (e.g. benzyl, phenethyl, nitrobenzyl, chlorobenzyl, trimethoxybenzyl, benzhydryl, p,p'-dimethoxydiphenylmethyl, pentachlorobenzyl, 4-oxy-3,5-di-tertiary butylbenzyl, pyridylmethyl, quinolylmethyl esters), ester with hydroxylamine derivatives (e.g. esters with N-hydroxysuccinimide, dimethylhydroxylamine, acetone oxime), vinyl ester, and like esters; the pharmaceutically acceptable cation can be alkali metal (e.g. lithium, sodium, potassium), alkaline earth metal (e.g. magnesium, calcium, barium), aluminum, organic base ions (e.g. trimethylammonium, triethyl-ammonium, tetramethylammonium, pyridinium, collidinium, quinolinium); tin or silyl esters, and the like.

As are exemplified above, the acyl group shown by Acyl, the hydrocarbyl group shown $R^1$, the acyl group shown by $R^2$, and the ester group shown by $R^3$ can, where possible, be further unsaturated, or interrupted by a hetero atom in its main chain, or substituted by halogen (e.g. fluorine, chlorine, bromine), nitrogen function (e.g. amino, hydrazinyl, azido, alkylamino), arylamino, acylamino, alkylideneamino, acylimino, imino, nitro), oxygen function (e.g. hydroxy, alkoxy, aralkoxy, aryloxy, acyloxy, oxo), sulfur function (mercapto, alkylthio, aralkylthio, arylthio, acylthio, thioxo, sulfo, sulfonyl, sulfinyl, alkoxysulfonyl, aryloxysulfinyl), carbon function (e.g. alkyl, alkenyl, aralkyl, aryl, carboxy, carbalkoxy, carbamoyl, alkanoyl, aroyl, aralkanoyl, cyano), phosphorous function (e.g. phospho, alkoxyphosphonyl), and other substituents containing up to 10 carbon atoms. When some of above groups show adverse changes during preparation, they can be protected prior to the reaction, and deprotected afterwards, according to a method conventional in the art.

Specific examples of the compound I are listed below:

methyl 7β-(2-thienylacetamido)-3-(1-iodomagnesiooxyethyl)-2-cephem-4-carboxylate [including two isomers]
diphenylmethyl 7β-(2-thienylacetamido)-3-(1-iodomagnesiooxyethyl)-2-cephem-4-carboxylate,
diphenylmethyl 7β-(2-thienylacetamido)-3-(1-iodomagnesiooxyethyl)-3-cephem-4-carboxylate,
diphenylmethyl 7β-(2-thienylacetamido)-3-(1-iodomagnesiooxyethyl)-3-cephem-4-carboxylate 1-oxide,
diphenylmethyl 7β-(2-thienylacetamido)-3-(1-lithiooxyethyl)-2-cephem-4-carboxylate,
methyl 7β-(2-thienylacetamido)-3-(1-hydroxyethyl)-2-cephem-4-carboxylate,
diphenylmethyl 7-(2-thienylacetamido)-3-(1-hydroxyethyl)-2-cephem-4-carboxylate,
diphenylmethyl 7β-(2-thienylacetamido)-3-(1-hydroxyethyl)-3-cephem-4-carboxylate,
diphenylmethyl 7β-(2-thienylacetamido)-3-(1-hydroxyethyl)-3-cephem-4-carboxylate 1-oxide,
7β-(2-thienylacetamido)-3-(1-acetoxyethyl)-3-cephem-4-carboxylic acid and its sodium salt or collidine salt,
diphenylmethyl 7β-(2-thienylacetamido)-3-(1-acetoxyethyl)-2-cephem-4-carboxylate,
diphenylmethyl 7β-(2-thienylacetamido)-3-(1-acetoxyethyl)-3-cephem-4-carboxylate, stereoisomers A and B,
diphenylmethyl 7β-(2-thienylacetamido)-3-(1-acetoxyethyl)-3-cephem-4-carboxylate 1-oxide, stereoisomers A and B,
7β-(2-thienylacetamido)-3-(1-benzoyloxyethyl)-3-cephem-4-carboxylic acid and its sodium salts, and benzylamine salt,
diphenylmethyl 7β-(2-thienylacetamido)-3-(1-benzoyloxyethyl)-2-cephem-4-carboxylate,
diphenylmethyl 7β-(2-thienylacetamido)-3-(1-benzoyloxyethyl)-3-cephem-4-carboxylate, stereoisomers A and B,
diphenylmethyl 7β-(2-thienylacetamido)-3-(1-benzoyloxyethyl)-3-cephem-4-carboxylate 1-oxide, stereoisomers A and B,
diphenylmethyl 7β-(2-thienylacetamido)-7α-methoxy-3-(1-acetoxyethyl)-2-cephem-4-carboxylate,
diphenylmethyl 7β-phenoxyacetamido-3-(1-acetoxyethyl)-3-cephem-4-carboxylate,
diphenylmethyl 7β-(2-thienylacetamido)-3-(α-bromomagnesiooxybenzyl)-2-cephem-4-carboxylate,
diphenylmethyl 7β-(2-thienylacetamido)-3-(α-bromomagnesiooxybenzyl)-3-cephem-4-carboxylate,
diphenylmethyl 7β-(2-thienylacetamido)-3-(α-hydroxybenzyl)-2-cephem-4-carboxylate, stereoisomers A and B,
7β-(2-thienylacetamido)-3-(α-acetoxybenzyl)-3-cephem-4-carboxylic acid,
diphenylmethyl 7β-(2-thienylacetamido)-3-(α-acetoxybenzyl)-2-cephem-4-carboxylate, stereoisomers A and B,
diphenylmethyl 7β-(2-thienylacetamido)-3-(α-acetoxybenzyl)-3-cephem-4-carboxylate, stereoisomers A and B,
diphenylmethyl 7β-(2-thienylacetamido)-3-(α-acetoxybenzyl)-3-cephem-4-carboxylate 1α-oxide, stereoisomers A and B,
diphenylmethyl 7β-(2-thienylacetamido)-3-(α-acetoxybenzyl)-3-cephem-4-carboxylate 1β-oxide, stereoisomers A and B,
7β-(2-thienylacetamido)-3-(1-hydroxyethyl)-3-cephem-4-carboxylic acid lactone,
7β-(2-thienylacetamido)-3-(1-hydroxyethyl)-3-cephem-4-carboxylic acid lactone 1-oxide,
7β-(2-thienylacetamido)-3-(α-hydroxybenzyl)-3-cephem-4-carboxylic acid lactone, stereoisomers A and B,
p-nitrobenzyl 7β-phenoxyacetamido-3-(1-bromomagnesiooxyethyl)-2-cephem-4-carboxylate,
p-nitrobenzyl 7β-phenoxyacetamido-3-(1-hydroxyethyl)-2-cephem-4-carboxylate,
p-nitrobenzyl 7β-phenoxyacetamido-3-(1-acetoxyethyl)-2-cephem-4-carboxylate,
p-nitrobenzyl 7β-phenoxyacetamido-3-(1-acetoxyethyl)-3-cephem-4-carboxylate 1-oxide,
p-nitrobenzyl 7β-phenoxyacetamido-3-(1-acetoxyethyl)-3-cephem-4-carboxylate,
7β-phenoxyacetamido-3-(1-acetoxyethyl)-3-cephem-4-carboxylic acid,
p-nitrobenzyl 7β-phenoxyacetamido-7α-methoxy-3-(1-acetoxyethyl)-3-cephem-4-carboxylate
7β-phenoxyacetamido-7α-methoxy-3-(1-acetoxyethyl)-3-cephem-4-carboxylic acid,
7β-amino-3-(1-acetoxyethyl)-3-cephem-4-carboxylic acid, and
p-nitrobenzyl 7β-phenoxyacetamido-3-(1-magnesiooxybutyl)-3-cephem-4-carboxylate.

The compounds can be prepared according to the methods disclosed below:

(1) The treatment of a 3-formylcephem compound with an organometal hydrocarbyl introducing reagent gives a compound I where $R^2$ is a metal or halometal group. The 3-formylcephem compound can be prepared easily from the corresponding 3-hydroxymethylcephem compounds by the action of hexavalent chromium oxidizing reagents. The organometal hydrocarbyl introducing reagents include the reagents forming a carbinol compound by the reaction with a carbonyl compound by introducing a hydrocarbyl group $R^1$, e.g. hydrocarbyl alkali metal (methyllithium, ethylsodium, butyllithium, phenyllithium, etc.), Grignard reagents (alkylmagnesium halide, arylmagnesium halide, aralkylmagnesium halide, etc.), organozinc and organocadmium compounds available for such reactions. This reaction is a conventional method for using organometallic hydrocarbyl introducing reagent, which can be carried out according to conventional methods e.g. under exclusion of moisture; in an inert solvent (e.g. ethers, hydrocarbons); and if required in the presence of iodine. It was surprising that the organometallic hydrocarbyl introducing reagent attacked preferentially at the 3-formyl group and not at the reactive carbonyl at position 8, that linked to position 4, or that which forms the amide at position 7, giving the desired compound. The produced metaloxy group is the group formed by combining the metal atom of the organometallic hydrocarbyl introducing reagent with the oxygen of the formyl group. The product can be isolated as a solid by separating the precipitate in the reaction medium or by adding non-polar solvent to the reaction mixture. When the product is brought into contact with a compound having active hydrogen e.g. water, alcohol, the following reaction (2) takes place to give the corresponding compound I where $R^2$ is a hydrogen.

(2) Treatment of a product of above reaction (1) with a reagent having an active hydrogen gives a corresponding compound I where $R^2$ is a hydrogen. The reagent having an active hydrogen can be water, acid, alcohol, and like compounds carrying a reactive hydrogen or a reagent capable of forming a corresponding hydroxy compound from the starting metaloxy compound.

(3) Treatment of a product of the above reaction (2) with an acylating reagent gives a corresponding compound I where $R^2$ is an acyl. The said acylating reagent is a conventional acylating reagent having desired acyl radical represented by Acyl in formula (I),e.g. acid, acid anhydride, acid halide, reactive amide, reactive ester, and like forms, if required in the presence of suitable condensing reagents e.g. N,N'-dicyclohexylcarbodiimide, 1-ethoxycarbonyl-2-ethoxy-1,2-dihydroquinoline, under specific conditions conventional for the reagent utilized.

(4) Treatment of a compound I where n is zero with an oxidizing reagent gives the corresponding 1-oxide where n is one. The said oxidizing reagent can be an oxidizing reagent capable of oxidizing a sulfide to give the corresponding 1-oxide, e.g. organic or inorganic peracids (e.g. perbenzoic acids, peralkanoic acids, periodic acid) and their salts, hydrogen peroxide, ozone, metal oxides, etc., preferably these forming less sulfone by-product. If required, the formation of the by-product sulfone can be surpressed by the addition of alcohols to the reaction medium. This reaction is used to shift the double bond from position 2 to 3.

(5) Treatment of the 1-oxide being compound I where n is one with a reducing reagent gives a compound I where n is zero. The said reducing reagent can be that capable of reducing a 1-oxide to give the corresponding 1-sulfide, e.g. reducing inorganic salt (e.g. thiosulfate, iodide, divalent tin salt, ferrous salt, phosphorous trihalide, phosphine, other trivalent phosphorous reagents), hydride (e.g. sodium borohydride, lithium trialkoxyaluminum hydride), hydrogen (over metal catalyzer e.g. platinum, palladium, nickel), utilizable in a conventional manner.

(6) Removing the carboxy protecting group of a compound I protected at its carboxy by conventional methods gives a corresponding compound I having free carboxy. The said conventional removal of carboxy protecting group are known for specific protecting groups, which includes hydrolyzing reagent (water in the presence of a catalyzer e.g. acid, base), reducing reagent (for haloalkyl ester, e.g. zinc, tin), hydrogenolysis using hydrogen (for aralkyl ester), and other methods for ester, amide, halide, anhydride, etc.

Salts can give free acid by cation exchange.

(7) Introduction of a carboxy protecting group into a compound I having free carboxy gives a compound protected at its carboxy. The methods for introduction of carboxy protecting groups are known for specific groups to be introduced. For example, esterification requires alcohol, phenol, or its reactive derivatives (e.g. diazo compound, halogen compound, reactive ester, reactive amide), or other esterifying reagent; amidation requires amine compounds, hydrazine compounds, reactive amide, etc.; cation exchange for salt formation; silyl halide, disilazane, tin halide, etc., for metallic esters. The said carboxy can be activated prior to the reaction e.g. by the action of an acid halide forming reagent (e.g. thionyl halide, phosphorous halide), acylating reagent (for producing anhydride e.g. alkyl haloformate in the presence of a base), amidating reagent (for making reactive amide e.g. carbonyl diimidazole) esterifying reagent (for making reactive ester e.g. p-nitrophenyl), or other reagents.

(8) Treatment of a compound I where Acyl corresponds to hydrogen with an acylating reagent gives the 7-acylamino derivative I. The acid acylating reagent can be a conventional acylating reagent having the desired acyl group shown by Acyl in formula (I) e.g. acid or its halide, anhydride, reactive ester, reactive amide, azide, or like acylating reagents. The starting amino can be activated in the form iminohalide, iminoether, isocyanate, or silylated amino prior to the reaction.

(9) The acyl group at position 7 represented by Acyl can be removed by conventional deacylation preferably by the iminohalide formation with e.g. phosphorous pentahalide, iminoether formation with alcohols, and hydrolysis with acid and water. The formed 7-amino compound can be used for the acylation given above (8).

(10) Lactone formation from the compound I where both of $R^2$ and $R^3$ are hydrogen can be done by keeping the hydroxyacid under neutral to acid condition even in aqueous medium of pH 1 to 7 or by the action of dehydrating reagents. Side reaction to give the lactone often lower the yield of desired products in reactions given above. The lactones also can be subjected to reactions (3) to (9).

The said reactions can be carried out preferably in an inert solvent, under cooling, heating or at room temperature. The product can be isolated by conventional methods e.g. extraction, absorption, precipitation, crystallization, etc., and purified by conventional methods e.g. recrystallization, chromatography, lyophilization, etc.

The compounds prepared by the said reactions are antibacterials useful for antibacterial drugs and can also be useful as intermediates for synthesis of other useful antibacterials. For human medical use, the compounds where $R^3$ is a hydrogen or pharmaceutically acceptable cation are given to the patient at a daily dose of 1 to 10 grams by enteral or parentheral administration in the forms of conventional pharmaceutical preparations. The compounds where $R^3$ is an ester residue are conventional starting materials for preparing the medically useful compounds where $R^3$ is a hydrogen or pharmaceutically acceptable cation.

The following examples illustrate the present invention. In the examples, EtOH is for ethanol; and DMSO is for dimethyl sulfoxide. The elemental analyses of the products give satisfactory results when compared with the calculated values. In the reactions, stereoisomers can be formed at the α-substituent of the 3-substituent, which can be separated by conventional methods. In the following examples, the descriptions referred to as the stereoisomer mean the stereoisomer derived from isomerism at position α of the substituent at position 3.

[A] Introduction of hydrocarbyl group.

EXAMPLE A1

To a stirred solution of diphenylmethyl 7-(2-thienylacetamido)-3-formyl-2-cephem-4-carboxylate (1.556 g) in a mixture of tetrahydrofuran (30 ml) and toluene (30 ml) is added a solution of methylmagnesium iodide (1.853 mM/ml) in ether (13 ml) during 4 minutes at −40° C. After 15 minutes, the reaction mixture contanig diphenylmethyl 7-(2-thienylacetamido)-3-(1-iodomagnesium oxyethyl)-2-cephem-4-carboxylate is poured into an aqueous saturated solution of ammonium chloride (30 ml), and is extracted with acetate. The extract solution is washed with saturated saline, dried over sodium sulfate, and evaporated under reduced pressure to give diphenylmethyl 7-(2-thienylacetamido)-3-(1-hydroxyethyl)-2-cephem-4-carboxylate, IR: $\nu_{max}^{CHCl_3}$ 3400, 3350, 1780, 1750, 1685, 1505 cm$^{-1}$. The product is dissolved in pyridine (16 ml), and is mixed with acetyl chloride (0.47 ml) under ice cooling. After 35 minutes, the reaction mixture is decomposed with a small amount of ice, poured into water after 10 minutes, and is stirred with ethyl acetate under ice cooling. The solution is neutralized with 4N-hydrochloric acid to pH 2.5, and is extracted with ethyl acetate. The extract solution is washed with saturated saline, dried over sodium sulfate, and evaporated under reduced pressure. Purification of the residue (1.66 g) by chromatography over silica gel (68 g) gives from fractions eluted with a mixture of benzene and ethyl acetate (6:1) diphenylmethyl 7-(2-thienylacetamido)-3-(1-acetoxyethyl)-2-cephem-4-carboxylate (625 mg: a mixture of stereoisomers). Colorless amorphous powder. Yield: 36.3%. NMR: $\delta^{CDCl_3}$ 1.21d(7.3Hz)3H, 1.73s+1.83s3H, 3.80s2H, 5.0–5.6m4H, 6.38br-s1H, 6.9–7.4m4H. IR: $\nu_{max}^{CHCl_3}$ 3400, 1782, 1746, 1690, 1502 cm$^{-1}$.

EXAMPLE A2

To a stirred solution of diphenylmethyl 7-(2-thienylacetamido)-3-formyl-2-cephem-4-carboxylate (1.297 g) in a mixture of tetrahydrofuran (26 ml) and toluene (26 ml) is added dropwise a solution of methylmagnesium iodide (1.853 mM/ml) in ether (10.8 ml) at −35° C during about 4 minutes. After 15 minutes, the reaction mixture containing diphenylmethyl 7-(2-thienylacetamido)-3-(1-iodomagnesiooxy)ethyl-2-cephem-4-carboxylate is poured into a mixture of saturated aqueous solution of ammonium chloride and ice water, and is extracted with ethyl acetate. The extract solution is washed with aqueous saturated saline, dried over sodium sulfate, and evaporated under reduced pressure. The obtained residue (1.296 g) is diphenylmethyl 7-(2-thienylacetamido)-3-(1-hydroxyethyl)-2-cephem-4-carboxylate, IR: $\nu_{max}^{CHCl_3}$ 3400, 3350, 1780, 1750, 1685, 1505 cm$^{-1}$. The residue is dissolved in pyridine, (13 ml), mixed dropwise with benzoyl chloride (0.48 ml) under ice cooling, allowed to stand for 35 minutes, mixed with ice, allowed to stand for 10 minutes, poured into ice water, and is extracted with ethyl acetate. The extract solution is washed with diluted hydrochloric acid, diluted aqueous solution of sodium hydrogen carbonate, and saturated saline, dried over sodium sulfate, and evaporated. The residue (1.606 g) is dissolved in benzene, freed from insoluble 7-(2-thienylacetamido)-3-(1-hydroxyethyl)-3-cephem-4-carboxylic acid (4-3')lactone (37 mg) [m.p. 239°–241° C (with decomposition); IR: $\nu_{max}^{KBr}$ 3260, 3070, 1788, 1760, 1662, 1562 cm$^{-1}$. NMR: $\delta^{d_6-DMSO}$ 1.41d(7Hz)3H, 3.76s2H, 5.10d(5Hz)1H, 5.27d(7Hz)1H, 5.82dd(8;5Hz)1H, 6.85–7.45m3H, 9.09d(8Hz)1H], and the filtrate is purified by chromatography over silica gel (60 g) to give diphenylmethyl 7-(2-thienylacetamido)-3-(1-benzoyloxyethyl)-2-cephem-4-carboxylate (a mixture of stereoisomers: 787 mg). Yield: 49.2%. Foam. NMR: $\delta^{CDCl_3}$ 1.32d(7Hz)3H, 3.78s2H, 5.1–5.9 m4H, 6.4–8.1m20H.

EXAMPLE A3

To a solution of diphenylmethyl 7-(2-thienylacetamido)-3-formyl-2-cephem-4-carboxylate (51.8 mg) in tetrahydrofuran (1 ml) is added a solution of methyllithium (1.6 mM/ml) in ether (0.5 ml) under argon atmosphere at −70° C. After 30 minutes, the reaction mixture containing diphenylmethyl 7-(2-thienylacetamido)-3-(1-lithiooxyethyl)-2-cephem-4-carboxylate is diluted with saturated aqueous ammonium chloride (3 ml), and is extracted with ethyl acetate. The extract solution is washed with saturated saline, dried over sodium sulfate, and evaporated to give yellow brown oil (51 mg). The oil is shown to be a mixture of 7-(2-thienylacetamido)-3-(1-hydroxyethyl)-3-cephem-4-carboxylic acid (4–3')-lactone, IR: $\nu_{max}^{KBr}$ 3260, 3070, 1788, 1760, 1662, 1562 cm$^{-1}$, and two stereoisomers of diphenylmethyl 7-(2-thienylacetamido)-3-(1-hydroxyethyl)-2-cephem-4-carboxylate, IR: $\nu_{max}^{CHCl_3}$ 3400, 3350, 1780, 1750, 1685, 1505 cm$^{-1}$. NMR: $\delta^{CDCl_3}$ 1.12d(7Hz)3H, 2.43br-s1H, 3.73s2H, 4.20q(7Hz)1H, 5.07d(4Hz)1H, 5.03s+5.23s1H, 5.45dd(8.5; 4Hz)1H, 6.17s+6.25s1H, 6.85s+6.92s1H, 6.8–7.4m13H, when examined on athin-layer chromatogram.

EXAMPLE A4 a. To a solution of diphenylmethyl 7-(2-thienylacetamido)-3-formyl-3-cephem-4-carboxylate (2.07 g) in a mixture of tetrahydrofuran (40 ml) and toluene (40 ml) is added a solution of phenylmagnesium bromide (2.0 mM/ml) in ether (16 ml) under argon atmosphere at −30° C to −40° C. After 30 minutes, the reaction mixture containing diphenylmethyl 7-(2-thienylacetamido)-3-(α-bromomagnesiooxy)benzyl-2-cephem-4-carboxylate is poured into saturated aqueous ammonius chloride (40 ml), and is extracted with ethyl acetate. The extract solution is washed with water, dried over sodium sulfate, and evaporated to leave yellow oil (2.5 g). Purification of the oil by chromatography over silica gel gives from the fraction eluted with a mixture of benzene and ethyl acetate (4:1) stereoisomers of diphenylmethyl 7-(2-thienylacetamido)-3-(α-hydroxybenzyl)-2-cephem-4-carboxylate (non-polar isomer A: 552 mg (23.2%); polar isomer B: 476 mg (20.0%) and stereoisomers of 7-(2-thienylacetamido)-3-(α-hydroxybenzyl)-3-cephem-4-carboxylic acid (4–3')-lactone (86 mg; 3.6%). Stereoisomer A: IR: $\nu_{max}^{CHCl_3}$ 3605, 3405, 1779, 1744, 1686, 1600, 1510 cm$^{-1}$. NMR: $\delta^{CDCl_3}$ 3.72s2H, 4.80s1H, 5.07d(4.5Hz)1H, 5.15brs 1H, 5.40dd(8.5;4.5Hz)1H, 6.45s1H, 6.73d(8.5Hz)1H, 6.78s1H, 7.1–7.4m--H.

Stereoisomer B: IR: $\nu_{max}^{CHCl_3}$ 3605, 3405, 1779, 1742, 1687, 1602, 1509 cm$^{-1}$. NMR: $\delta^{CDCl_3}$ 3.7s2H, 5.08d(4.5Hz)1H, 5.22br-s1H, 5.37s1H, 5.42dd(8;4.5Hz)1H, 5.83s1H. $[\alpha]_D^{24.5}$ +273.9° (c=0.498, CHCl$_3$).

b. To a solution of diphenylmethyl 7-(2-thienylacetamido)-3-formyl-2-cephem-4-carboxylate (10.36 g) in a mixture (400 ml) of tetrahydrofuran and toluene (1:1) is added dropwise a solution of phenylmagnesium bromide (1.56 mM/ml) in ether (103 ml) under nitrogen atmosphere at −50° C to −60° C. After 45 minutes, the reaction mixture containing diphenylmethyl 7-(2-thienylacetamido)-3-(α-bromomagnesiooxy)benzyl-2-cephem-4-carboxylate is diluted with saturated aqueous solution of ammonium chloride (200 ml), and is extracted with ethyl acetate. The extract solution is washed with water, dried over sodium sulfate, and evaporated. The obtained residue (13 g; yellow-brown oil) is chromatographed over silica gel containing 10% water using a mixture of benzene and ethyl acetate (4:1) as developing solvent to give diphenylmethyl 7-(2-thienylacetamido)-3-(α-hydroxy)benzyl-2-cephem-4-carboxylate (stereoisomer A: 2.0 g; (17%); stereoisomer B: 2.0 g (17%); a mixture of A and B: 2.2 g (18.5%)), diphenylmethanol 1.2 g (33%; and stereoisomers of 7-(2-thienylacetamido)-3-(α-hydroxy)benzyl-3-cephem-4-carboxylic acid (4–3')-lactone (A: 350 mg (3.0%); B 350 mg (4.2%)). Stereoisomer A of the lactone: m.p. 226°–229° C (with decomposition). IR: $\nu_{max}^{Nujol}$ 3265, 1800, 1794, 1762, 1655, 1523 cm$^{-1}$. UV: $\lambda_{max}^{EtOH}$ 239 nm (ε=12700); 258 nm (ε=9900). $[\alpha]_D^{23}$ +121.4° (c=0.491, CHCl$_3$). NMR: $\delta^{d6-DMSO}$ 3.39+3.83ABq(18Hz)2H, 3.80s2H, 5.17d(5Hz) 1H, 5.88dd(8;5Hz)1H, 6.32s1H, 6.9–7.5m8H, 9.15d(8Hz)1H. Streoisomer B of the lactone: m.p. 197°–202° (with decomposition). IR: $\nu_{max}^{Nujol}$ 3275, 1803, 1768, 1649, 1511 cm$^{-1}$. UV: $\lambda_{max}^{EtOH}$ 239 nm (ε=12300); 258 nm (ε=8600). $[\alpha]_D^{25}$ −26.0° (c=0.412, CHCl$_3$). NMR: $\delta^{d6-DMSO}$ 3.08+3.87ABq(18Hz)2H, 3.76s2H, 5.18d(5Hz)1H, 5.92dd(9;5Hz)1H, 6.30s1H, 6.85–7.60m8H, 9.19d(9Hz)1H.

EXAMPLE A5

To a solution of diphenylmethyl 7-(2-thienylacetamido)-3-(α-hydroxybenzyl)-2-cephem-4-carboxylate (stereoisomer A; 503 mg) in pyridine (6 ml) is added dropwise acetyl chloride (130 μl) under ice cooling. After 45 minutes, the reaction mixture is decomposed with ice, stirred for 10 minutes, poured into ice water, and is extracted with ethyl acetate. The ethyl acetate layer is washed with 2N-hydrochloric acid and water, dried over sodium sulfate, and evaporated under reduced pressure. Purification of the residue (567 mg) by chromatography over silica gel containing 10% water gives from the fraction eluted with a mixture of benzene and ethyl acetate (4:1) diphenylmethyl 7-(2-thienylacetamido)-3-(α-acetoxybenzyl)-2-cephem-4-carboxylate (498 mg: Stereoisomer A). Yield: 93%. IR: $\nu_{max}^{CHCl_3}$ 3690, 3405, 1781, 1744, 1683, 1602, 1509 cm$^{-1}$. UV: $\lambda_{max}^{EtOH}$ 237 nm (ε=15700). $[\alpha]_D^{24.5}$ +280° (c=0.486, CHCl$_3$). NMR: $\delta^{CDCl_3}$ 1.85s3H, 3.80s2H, 4.82-1H, 5.08d(4Hz)1H, 5.47dd(9;4Hz)1H, 6.30s1H, 6.35s1H, 6.60d(9Hz)1H, 6.82s1H, 7.2–7.5m--H.

In a procedure similar to these as described above, diphenylmethyl 7-(2-thienylacetamido)-3-(α-hydroxybenzyl)-2-cephem-4-carboxylate (stereoisomer B: 400 mg) is converted into the corresponding diphenylmethyl 7-(2-thienylacetamido)-3-(α-acetyloxybenzyl)-2-cephem-4-carboxylate (stereoisomer B: 417 mg). Yield: 97.5%. IR: $\lambda_{max}^{CHCl_3}$ 3410, 1780, 1744, 1687, 1509, 1499 cm$^{-1}$. UV: $\lambda_{max}^{EtOH}$ 241nm (ε=14200). $[\alpha]_D^{25}$ +321.6° (c=0.445, CHCl$_3$). NMR: $\delta^{CDCl_3}$ 1.88s3H, 3.78s2H, 5.13d(4Hz)1H, 5.17br-s1H, 5.53dd(9;4Hz)1H, 5.97s1H, 6.38s1H.

EXAMPLE A6

To a solution of diphenylmethyl 7-(2-thienylacetamido)-3-formyl-3-cephem-4-carboxylate 1-oxide (53.5 mg) in tetrahydrofuran (3 ml) is added a solution of methylmagnesium iodide (1.853mM/ml) in ether (0.43 ml) at −30° to −35° C. After 20 minutes, the reaction mixture containing diphenylmethyl 7-(2-thienylacetamido)-3-(1-iodomagnesiooxy)ethyl-3-cephem-4-carboxylate 1-oxide is diluted with saturated aqueous ammonium chloride (2 ml) and is extracted with ethyl acetate. The extract solution is washed with saline, dried over sodium sulfate, and evaporated. A thin-layer chromatogram of the residue (42 mg) shows spots of diphenylmethyl 7-(2-thienylacetamido)-3-(1-hydroxyethyl)-3-cephem-4-carboxylate 1-oxide (Rf: 0.45) and 7-(2-thienylacetamido-3-(1-hydroxyethyl)-3-cephem-4-carboxylic acid (4–3')-lactone 1-oxide (Rf: 0.05) (a mixture of benzene and ethyl acetate (1:1) over silica gel). The main product is inferred to be the lactone from the thin-layer chromatogram.

EXAMPLE A7

To a solution of diphenylmethyl 7-(2-thienylacetamido)-3-formyl-3-cephem-4-carboxylate (53 mg) in a mixture in tetrahydrofuran (1 ml) and toluene (1 ml) is added dropwise a solution of methylmagnesium iodide (1.853 mM/ml) in ether (0.43 ml) at −30° to −35° C. After 20 minutes, the reaction mixture containing diphenylmethyl 7-(2-thienylacetamido)-3-(1-iodomagnesiooxy)ethyl-3-cephem-4-carboxylate is mixed with a saturated aqueous solution of ammonium chloride (2 ml), diluted with ice water, and is extracted with ethyl acetate. The extract solution is washed with water, dried over sodium sulfate, and evaporated to leave residue (48 mg). The thin-layer chromatogram of the residue shows the presence of diphenylmethyl 7-(2-thienylacetamido)-3-(1-hydroxyethyl)-3-cephem-4-carboxylate (Rf: 0.40) and 7-(2-thienylacetamido)-3-(1-hydroxyethyl)-3-cephem-4-carboxylic acid (4–3')-lactone (Rf: 0.05) (a mixture of benzene and ethyl acetate (1:1)/silica gel).

EXAMPLE A8

To a solution of methyl 7-(2-thienylacetamido)-3-formyl-2-cephem-4-carboxylate (550 mg) in a mixture of tetrahydrofuran (11 ml) and toluene (11 mg) is added dropwise a solution of methylmagnesium iodide (1.853 mM/ml) in ether (6.5 ml) at −45° C under nitrogen atmosphere. After 30 minutes, the reaction mixture containing methyl 7-(2-thienylacetamido)-3-(1-iodomagnesiooxyethyl)-2-cephem-4-carboxylate is mixed with saturated aqueous ammonium chloride (25 ml), and is extracted with ethyl acetate. The extract solution is washed with water and saturated saline, dried over sodium sulfate, and evaporated. The residue (582 mg) gives by crystallization from a mixture of methylene chloride and ether 7-(2-thienylacetamido)-3-(1-hydroxyethyl)-3-cephem-4-carboxylic acid (4–3')-lactone (70 mg). Yield: 13.9%. m.p. 239°–241° C (with decomposition). The mother liquor is evaporated, and the resulted residue is washed with ether to give a mixture of stereoisomers of methyl 7-(2-thienylacetamido)-3-(1-hydroxyethyl)-2-cephem-4-carboxylate (410 mg). IR: $\nu_{max}^{CHCl_3}$ 3405, 1780, 1755, 1681, 1500 cm$^{-1}$. NMR: $\delta^{CDCl_3}$ 1.29d(7Hz)3H, 3.80s3H, 3.90s2H, 4.40q(7Hz)1H, 5.03br-s1H, 5.23d(7Hz)1H, 5.60q(8;4Hz) 1H, 6.33br-1H, 6.9–7.4m--H.

[B] Preparation of sulfoxides

EXAMPLE B1

To a solution of a mixture of stereoisomers of diphenylmethyl 7-(2-thienylacetamido)-3-(1-acetoxyethyl)-2-cephem-4-carboxylate (611 mg) in a mixture of methylene chloride (6 ml) and isopropanol (6 ml) is added under stirring a solution of m-chloroperbenzoic acid (274 mg) in a mixture of methylene chloride (1.3 ml) and isopropanol (1.3 ml) under ice cooling. After 20 minutes, the reaction mixture is diluted with methylene chloride, washed with a solution of sodium hydrogen carbonate and saturated saline, dried over sodium sulfate, and evaporated under reduced pressure. Purification of the residue (696 mg) by chromatography over silica gel (70 g) gives from the fraction eluted with a mixture of benzene and ethyl acetate (4:1 to 3:2) the stereoisomers A and B of diphenylmethyl 7-(2-thienylacetamido)-3-(1-acetoxyethyl)-3-cephem-4-carboxylate 1-oxide, partly separated by the said chromatography.

Non-Polar stereoisomer A: m.p. 112°–117° C. Yield: 18.6%. Crop: 117 mg. IR: $\nu_{max}^{CHCl_3}$ 3381, 1803, 1732, 1689, 1510 cm$^{-1}$. $[\alpha]_D^{24}$ +17.4° (c=0.459, CHCl$_3$). NMR: $\delta^{CDCl_3}$ 1.33d(6.5Hz)3H, 1.97s3H, 2.93d(19Hz)1H, 3.82d(19Hz)1H, 3.83s2H, 4.40d(4.5Hz)1H, 6.01q(10;4.5Hz)1H, 6.08q(6.5Hz)1H, 6.7–7.5m15H. Polar stereoisomer B: m.p. 105°–112° C. Yield: 13.2%. Crop: 83 mg. IR: $\nu_{max}^{CHCl_3}$ 3384, 1803, 1734, 1689, 1509 cm$^{-1}$. $[\alpha]_D^{24}$ +41.9° (c=0.454, CHCl$_3$). NMR: $\delta^{CDCl_3}$ 1.23d(6.5Hz)3H, 1.88s3H, 3.1od(19Hz)1H, 3.83s2H, 3.87d(19Hz)1H, 4.41d(5Hz)1H, 6.00q(10;5Hz)1H, 6.12q(6.5Hz)1H, 6.8–7.5m15H. A mixture of the stereoisomers A and B: 256 mg. Yield: 40.7%.

EXAMPLE B2

To a solution of a mixture of stereoisomers of diphenylmethyl 7-(2-thienylacetamido)-3-(1-benzoyloxyethyl)-2-cephem-4-carboxylate (787 mg) in a mixture of methylene chloride (7 ml) and isopropanol (7 ml) is added a solution of m-chloroperbenzoic acid (346 mg) in a mixture of methylene chloride (1.7 ml) and isopropanol (1.7 ml). After 20 minutes, the reaction mixture is diluted with methylene chloride, washed with aqueous sodium hydrogen carbonate and saturated saline, dried over sodium sulfate, and evaporated. Purification of the residue (861 mg) by chromatography over silica gel (86 mg) gives from the fraction eluted with a mixture of benzene and ethyl acetate (6:1) a mixture of stereoisomers A and B of diphenylmethyl 7-(2-thienylacetamido)-3-(1-benzoyloxyethyl)-3-cephem-4-carboxylate 1-oxide.

Non-polar stereoisomer A: m.p. 193.5°–194.5° C. Yield: 37.2%. Crop: 300 mg. IR: $\nu_{max}^{CHCl_3}$ 3376, 1804, 1725, 1689, 1583, 1509 cm$^{-1}$. $[\alpha]_D^{23.5}$ +69.5° (c=0.509, CHCl$_3$). NMR: $\delta^{CDCl_3}$ 1.47d (6.5Hz)3H, 2.95d(18Hz)1H, 3.88d(18Hz)1H, 3.80s2H, 4.34d(5Hz)1H, 5.97q(9.5;5Hz)1H, 6.32q(6.5Hz)1H, 6.8–8.1m20H. Polar stereoisomer B: m.p. 207°–208° C. Crop: 167 mg. Yield: 20.7%. IR: $\nu_{max}^{CHCl_3}$ 3386, 1803, 1726, 1686, 1600, 1584, 1510 cm$^{-1}$. $[\alpha]_D^{23.5}$ −23.3° (c=0.524, CHCl$_3$). NMR: $\delta^{CDCl_3}$ 1.32d (6.5Hz)3H, 3.17d(18Hz)1H, 3.90d(18Hz)1H, 3.81s2H, 4.41d(5Hz)1H, 5.94q(9.5;5Hz)1H, 6.44q(6.5Hz)1H, 6.8–8.1m20H.

EXAMPLE B3

To a solution of stereoisomer A of diphenylmethyl 7-(2-thienylacetamido)-3-(α-acetyloxybenzyl)-2-cephem-4-carboxylate (468 mg) in a mixture (10 ml) of methylene chloride and isopropanol (1:1) is added a solution of 80% m-chloroperbenzoic acid (205 mg) in a mixture (2 ml) of methylene chloride and isopropanol (1:1) at 0° C. After 30 minutes, the reaction mixture is diluted with methylene chloride (120 ml), washed with aqueous sodium hydrogen carbonate and water, dried over sodium sulfate, and evaporated. From the residue are obtained the crystalline 1β-oxide and 1α-oxide of the stereoisomer A of diphenylmethyl 7-(2-thienylacetamido)-3-(α-acetyloxybenzyl)-3-cephem-4-carboxylate.

Stereoisomer A 1β-oxide: m.p. 135°–141° C. Crop: 424 mg. Yield: 89%. IR: $\nu_{max}^{CHCl_3}$ 3520, 3385, 2925, 2655, 2545, 1805, 1735, 1703, 1598, 1574, 1508, 1498 cm$^{-1}$. $[\alpha]_D^{25}$ −41.2° (c=0.485) CHCl$_3$). NMR: $\delta^{CDCl_3}$ 2.07s3H, 2.92d(19Hz)1H, 3.56d(19Hz)1H, 3.78s2H, 4.32d(5Hz)1H, 5.95dd(9.5;5Hz)1H, 6.8–7.4m19H, 6.89s1H, 7.18s1H. UV: $\lambda_{max}^{EtOH}$ 230 nm (ε=18600); 274 nm (ε=7800). Stereoisomer A 1α-oxide: m.p. 80–90° C. Crop: 50mg. Yield: 10.5%. IR: $\nu_{max}^{CHCl_3}$ 3390, 3210, 1808, 1730, 1690, 1570 cm$^{-1}$. NMR: $\delta^{CDCl_3}$ 2.08s3H, 3.43+3.92ABq(18Hz)2H, 3.80s2H, 4.82d(5Hz) 1H, 6.00s1H, 7.20s1H, 6.9–7.5m19H.

Similarly, from the stereoisomer B (345 mg) of diphenylmethyl 7-(2-thienylacetamido)-3-(α-acetoxybenzyl)-2-cephem-4-carboxylate are prepared the 1β-oxide and 1α-oxide of the stereoisomer B of diphenylmethyl 7-(2-thienylacetamido)-3-(α-acetoxybenzyl)-3-cephem-4-carboxylate. Stereoisomer B 1β-oxide: m.p. 115°–118° C. Crop: 285 mg. Yield: 82%. IR: $\nu_{max}^{CHCl_3}$ 3370, 1804, 1744, 1689, 1510, 1498 cm$^{-1}$. $[\alpha]_D^{25.5}$ +94.3° (c=0.453, CHCl$_3$). NMR: $\delta^{CDCl_3}$ 2.03s3H, 2.80+3.95ABq(18Hz)2H, 3.83s2H, 4.28d(5Hz)1H, 5.98dd(10;5Hz)1H, 6.93s1H, 6.9–7.5m. UV: $\lambda_{max}^{EtOH}$ 238 nm (ε=13000); 270 nm (ε=9200). Stereoisomer B 1α-oxide: yellow oil. Crop: 48 mg. Yield: 13.8%. IR: $\nu_{max}^{CHCl_3}$ 3390, 1810, 1735, 1690 cm$^{-1}$. NMR: $\delta^{CDCl_3}$ 2.05s3H, 3.52+4.00ABq(20Hz)2H, 3.82s2H, 4.62d(5Hz)1H, 6.03dd (10;5Hz)1H, 6.92s1H, 6.9–7.5m19H.

Similarly, from the stereoisomer A (71 mg) of diphenylmethyl 7-(2-thienylacetamido)-3-(α-acetyloxybenzyl)-3-cephem-4-carboxylate is prepared the 1β-oxide of the stereoisomer A of diphenylmethyl 7-(2-thienylacetamido)-3-(α-acetyloxybenzyl)-3-cephem-4- carboxylate, m.p. 135°–141° C. Crop: 55 mg. Yield: 76%.

[C] Reduction of sulfoxides

EXAMPLE C1

To a solution of non-polar stereoisomer A of diphenylmethyl 7-(2-thienylacetamido)-3-(1-acetoxyethyl)-3-cephem-4-carboxylate 1-oxide (85 mg) in N,N-dimethylformamide (2.5 ml) is added under ice cooling stannous chloride dihydrate (81 mg) with stirring. Ten minutes after the addition of acetyl chloride (0.34 mg), the mixture is stirred with ice for 20 minutes. The reaction mixture is poured into ice water, and is extracted with ethyl acetate. The extract solution is washed with aqueous sodium hydrogen carbonate and saline, dried over sodium sulfate, and evaporated. Recrystallization of the residue (81 mg) from petroleum ether gives the stereoisomer A of diphenylmethyl 7-(2-thienylacetamido)-3-(1-acetoxyethyl)-3-cephem-4-carboxylate (66 mg). m.p. 77°–85° C. Yield: 79.8%. IR: $\nu_{max}^{CHCl_3}$ 3405, 1789, 1728, 1685, 1509 cm$^{-1}$. NMR: $\delta^{CDCl_3}$ 1.34d(6.5Hz)3H, 1.98s3H, 3.37s2H, 3.82s2H, 4.96d(5Hz)1H, 5.79q(8.5;5Hz)1H, 5.99q(6.5Hz)1H, 6.32d(8.5Hz)1H, 6.8–7.5m14H.

Similarly, polar isomer B of diphenylmethyl 7-(2-thienylacetamido)-3-(1-acetoxyethyl)-3-cephem-4-carboxylate 1-oxide (69 mg) is reduced with stannous chloride dihydrate (66 mg) and acetyl chloride (0.28 ml) in N,N-dimethylformamide (2.1 ml) for 15 minutes to give stereoisomer B of diphenylmethyl 7-(2-thienylacetamido)-3-(1-acetoxyethyl)-3-cephem-4-carboxylate (71 mg). m.p. 72°–80° C. Yield: 83.4%. IR: $\nu_{max}^{CHCl_3}$ 3396, 1787, 1731, 1687, 1508 cm$^{-1}$. NMR: $\delta^{CDCl_3}$ 1.27d(6.5Hz) 3H, 1.88s3H, 3.40br-s2H, 3.83s2H, 4.95d(5Hz)1H, 5.72q(9;5Hz) 1H, 6.11q(6.5Hz)1H, 6.48d(9Hz)1H, 6.9–7.5m14H.

EXAMPLE C2

To a solution of diphenylmethyl 7-(2-thienylacetamido)-3-(1-benzoyloxyethyl)-3-cephem-4-carboxylate 1β-oxide (stereoisomer A: 282 mg) in N,N-dimethylformamide (8.4 ml) are added stannous chloride dihydrate (243 mg) and acetyl chloride (1.2 ml). After 15 minutes, ice is added to the reaction mixture, stirred for 10 minutes, poured into ice water, and is extracted with ethyl acetate. The extract solution is washed with aqueous sodium hydrogen carbonate solution and saline, dried over sodium sulfate, and evaporated. Purification of the residue (319 mg) by chromatography over silica gel (12 g) gives from the fraction eluted with a mixture of benzene and ethyl acetate (9:1) diphenylmethyl 7-(2-thienylacetamido)-3-(1-benzoyloxyethyl)-3-cephem-4-carboxylate (stereoisomer A: 203 mg). m.p. 161°–163° C. Yield: 73.7%. IR: $\nu_{max}^{CHCl_3}$ 3404, 1788, 1724, 1689, 1601, 1584, 1508 cm$^{-1}$. $[\alpha]_D^{24.5}$ +55.8° (c=0.346, CHCl$_3$). NMR: $\delta^{CDCl_3}$ 1.48d(6Hz)3H, 3.45s2H, 3.82s2H, 4.92d(4.5Hz)1H, 5.78q(8.5;4.5Hz)1H, 6.23q(6Hz)1H, 6.39d(8.5Hz)1H, 6.8–8.1m19H.

Similarly, the reaction of diphenylmethyl 7-(2-thienylacetamido)-3-(α-benzoyloxyethyl)-3-cephem-4-carboxylate 1β-oxide (stereoisomer B: 158 mg) in N,N-dimethylformamide (4.8 ml) with stannous chloride dihydrate (136 mg) and acetyl chloride (0.7 ml) at room temperature for 15 minutes gives diphenylmethyl 7-(2-thienylacetamido)-3-(1-benzyloxyethyl)-3-cephem-4-carboxylate (stereoisomer B: 119 mg). m.p. 129°–133° C. Yield 77.3%. IR: $\nu_{max}^{CHCl_3}$ 3400, 1788, 1724, 1688, 1601, 1584, 1509 cm$^{-1}$. $[\alpha]_D^{24.5}$ −36.6° (c=0.366, CHCl$_3$). NMR: $\delta^{CDCl_3}$ 1.38d(6.5Hz)3H, 3.52s2H, 3.82s2H, 4.97d(5Hz)1H, 5.74d(9;5Hz)1H, 6.51q(6.5Hz)1H, 6.59d(9Hz)1H, 6.8–8.1m19H.

EXAMPLE C3

To a solution of diphenylmethyl 7-(2-thienylacetamido)-3-(α-acetoxybenzyl)-3-cephem-4-carboxylate 1β-oxide (stereoisomer A: 328 mg) in N,N-dimethylformamide (9 ml) under nitrogen atmosphere are added stannous chloride dihydrate (282 mg) and acetyl chloride (1.25 ml) under ice cooling. After 30 minutes, the reaction mixture is mixed with ice, stirred for 5 minutes, poured into ice water, and is extracted with ethyl acetate. The extract solution is washed with aqueous sodium hydrogen carbonate solution and saline, dried over sodium sulfate, and evaporated. Crystallization of the residue from a mixture of methylene chloride and ether gives diphenylmethyl 7-(2-thienylacetamido)-3-(α-acetoxybenzyl)-3-cephem-4-carboxylate (stereoisomer A: 270 mg). m.p. 167°–170° C. Yield: 85%. IR: $\nu_{max}^{CHCl_3}$ 3400, 1787, 1732, 1690, 1632, 1602, 1510, 1499 cm$^{-1}$. UV: $\lambda_{max}^{EtOH}$ 237 nm (ε=13400); 266 nm (ε=8800). $[\alpha]_D^{25}$ −125.8° (c=0.457, CHCl$_3$). NMR: $\delta^{CDCl_3}$ 2.10s3H, 3.08+3.45ABq(18Hz)1H+1H, 3.77s2H, 4.97d(5Hz)1H, 5.80dd(8.5;5Hz)1H, 6.43d(8.5Hz) 1H, 6.90s1H, 7.20s1H.

Similar treatment of diphenylmethyl 7-(2-thienylacetamido)-3-(α-acetoxybenzyl)-3-cephem-4-carboxylate 1β-oxide (stereoisomer B: 240 mg) gives diphenylmethyl 7-(2-thienylacetamido)-3-acetoxybenzyl-3-cephem-4-carboxylate (stereoisomer B: 270 mg). Yellow oil. Nearly quantitative yield. IR: $\nu_{max}^{CHCl_3}$ 3405, 1788, 1745, 1688, 1509, 1499 cm$^{-1}$. UV: $\lambda_{max}^{EtOH}$ 238 nm (ε=13700); 267 nm (ε=8800). $[\alpha]_D^{24.5}$ +60.3° (c=0.478, CHCl$_3$). NMR: $\delta^{CDCl_3}$ 1.99s3H, 3.10+3.53ABq(18Hz)2H, 3.82s2H, 4.84d(5Hz)1H, 5.77d(9;5Hz)1H, 6.53d(9Hz)1H, 6.93s1H, 7.18s1H.

[D] Deprotection of carboxy protecting group.

EXAMPLE D1

To a solution of diphenylmethyl 7-(2-thienylacetamido)-3-(1-acetoxyethyl)-3-cephem-4-carboxylate (stereoisomer A: 58 mg) in methylene chloride (0.6 ml) are added anisole (0.12 ml) and trifluoroacetic acid (0.12 ml). After 15 minutes, the reaction mixture is concentrated at room temperature, and obtained residue is dissolved in ethyl acetate, and is extracted with aqueous sodium hydrogen carbonate solution. The extract aqueous solution is cooled with ice, stirred and neutralized with 1N-hydrochloric acid to pH 2, and is extracted with ethyl acetate. The extract solution is washed with water, dried over sodium sulfate, and concentrated to one third volume. To this solution is added an equivalent amount of collidine or benzylamine, and the separated crystals are collected by filtration to give 7-(2-thienylacetamido)-3-(1-acetoxyethyl)-3-cephem-4-carboxylic acid (stereoisomer A) collidine salt or benzylamine salt.

Collidine salt: crystallizes on cooling with ice. IR: $\nu_{max}^{CHCl_3}$ 3380, 1763, 1630, 1640 cm$^{-1}$.

EXAMPLE D2

To a solution of diphenylmethyl 7-(2-thienylacetamido)-3-(1-benzyloxyethyl)-3-cephem-4-carboxylate (stereoisomer A: 160 mg) in methylene chloride (1.6 ml) are added anisole (0.32 ml) and trifluoroacetic acid (0.32 ml). After 15 minutes, the reaction mixture is evaporated to dryness, and the obtained residue is dissolved in ethyl acetate. The solution is extracted with aqueous sodium hydrogen carbonate solution. The extract solution is evaporated with ethyl acetate, cooled with ice, stirred and neutralized with 1N-hydrochloric acid to pH 2.0, and is extracted with ethyl acetate. The extract solution is washed with saline, dried over sodium sulfate, and evaporated to give 7-(2-thienylacetamido)-3-(1-benzoyloxyethyl)-3-cephem-4-carboxylic acid (stereoisomer A: 60 mg). m.p. 114°–118° C. RF: same with the benzylamine salt described below.

The carboxylic acid (45 L mg) is dissolved in ethyl acetate (0.2 ml), mixed with benzylamine (12.5 μl), and kept under ice cooling over-night to give the benzylamine salt (26.5 mg). m.p. 110°–117° C. IR: $\nu_{max}^{CHCl_3}$ 3650, 3395, 1768, 1713, 1679, 1602 1513 cm$^{-1}$.

EXAMPLE D3

To a solution of diphenylmethyl 7-(2-thienylacetamido)-3-(α-acetyloxybenzyl)-3-cephem-4-carboxylate (stereoisomer A: 192 mg) in methylene chloride (5 ml) are added anisole (0.5 ml) and trifluoroacetic acid (0.5 ml) under ice cooling. After 2.5 hours, the reaction mixture is concentrated under reduced pressure, and diluted with a mixture of ether and pentane to crystallize 7-(2-thienylacetamido)-3-(α-acetyloxybenzyl)-3-cephem-4-carboxylic acid (stereoisomer A: 98 mg). m.p. 107°–110° C (with decomposition). Yield: 69%. IR: $\nu_{max}^{CHCl_3}$ 3290, 1755, 1739, 1672, 1632, 1525 cm$^{-1}$. UV: $\lambda_{max}^{EtOH}$ 238 nm (ε=12600); 267 nm (ε=7700), $[\alpha]_D^{25}$ −46.4° (c=0.470, CHCl$_3$). NMR: $\delta^{CDCl_3}$ 2.16s3H, 3.08+3.68ABq(17;8Hz)2H, 3.75s2H, 5.18d(4.5Hz)1H, 5.74dd(8.5;4.5Hz)1H, 6.13s1H, 6.85–7.60m, (1.10d(8.5Hz)1H)

[E] Acylation and the protection of carboxy group.

EXAMPLE E1

To a solution of diphenylmethyl 7-amino-3-(1-acetoxyethyl)-2-cephem-4-carboxylate (stereoisomer A: 90 mg) in methylene chloride (3 ml) containing triethylamine (50 mg) is added a solution of 2-thienylacethyl chloride (35 mg) in methylene chloride (0.35 ml). After 3 hours, the reaction mixture is washed with aqueous sodium hydrogen carbonate solution, hydrochloric acid, and water, dried over sodium sulfate, and evaporated. Recrystallization of the residue from a mixture of ether and petroleum ether gives diphenylmethyl 7-(2-thienylacetamido)-3-(1-acetoxyethyl)-2-cephem-4-carboxylate (stereoisomer A: 95 mg). Yield: 80%. m.p. 161°–163° C.

Similarly, treatment of diphenylmethyl 7-amino-3-(1-acetoxyethyl)-3-cephem-4-carboxylate (stereoisomer A) in methylene chloride with phenoxyacetyl chloride in the presence of triethylamine gives diphenylmethyl 7-phenoxyacetamido-3-(1-acetoxyethyl)-3-cephem-4-carboxylate (stereoisomer A).

EXAMPLE E2

To a solution of 7-(2-thienylacetamido)-3-(1-acetoxyethyl)-3-cephem-4-carboxylic acid (stereoisomer A: 88 mg) in mixture (5 ml) of methanol and methylene chloride (1:1) is added a solution of diphenyldiazomethane in ether until the red color of the solution does no more disappear at 55° C on standing. After 3 hours, the reaction mixture is concentrated to give the residue which is stirred in a mixture of ether and petroleum ether. The supernatant is removed, and resulting precipitate is recrystallized from petroleum ether to give diphenylmethyl 7-(2-thienylacetamido)-3-(1-acetoxyethyl)-3-cephem-4-carboxylate (stereoisomer A: 85 mg). m.p. 161-163° C. Yield: 70%.

What we claim is:

1. A compound of the formula:

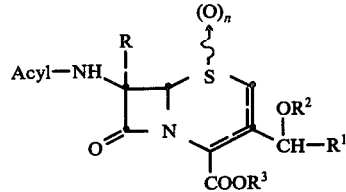

wherein
Acyl is selected from a group of acyls consisting of formyl, acetyl, butyryl, pivaloyl, cyclopentylcarbonyl, cyclohexylcarbonyl, cyclohexylacetyl, cycloheptylacetyl, dihydrophenylacetyl, crotonyl, methoxyacetyl, methylthioacetyl, isopropenylthioacetyl, phenoxyacetyl, phenylthioacetyl, benzyloxyacetyl, benzoyl, xylol, naphthoyl, phthaloyl, tetrahydronaphthoyl, nicotinoyl, pyrazinoyl, 2-methyl-5-phenylisoxazol-5-ylcarbonyl, phenylacetyl, phenylpropionyl, tolylacetyl, naphthylacetyl, tetrahydronaphthylacetyl, tetrazolylacetyl, thienylacetyl, thienylpropionyl, furylacetyl, pyrimidylacetyl, pyrrylacetyl, isoxazolylacetyl, benzoisothiazolylacetyl, benzoxazolylacetyl, cyclohexyloxycarbonyl, cycloheptyloxycarbonyl, benzyloxycarbonyl, phenoxycarbonyl, naphthyloxycarbonyl, pyridylmethoxycarbonyl, 2,2,2-trichloroethoxycarbonyl and cyclopropylethoxycarbonyl;

R is hydrogen or methoxy;

R$^1$ is alkyl of 1 to 8 carbon atoms, cycloalkyl of up to 8 carbon atoms, phenylalkyl of up to 8 carbon atoms, or phenyl;

R$^2$ is lithium, sodium, potassium, magnesium, cadmium, zinc, chloromagnesium, bromomagnesium, iodomagnesium, bromozinc or bromocadmium;

R$^3$ is hydrogen, a pharmaceutically acceptable cation, or an ester residue selected from the group of methyl, ethyl, t-butyl, cyclohexyl, propenyl, methoxymethyl, ethoxymethyl, methylthioethyl, phenoxymethyl, phenylthiomethyl, tolylmethyl, chloromethyl, bromomethyl, trichloroethyl, cyanomethyl, nitrophenylthiomethyl, chlorophenoxymethyl, chlorophenacyl, nitrophenacyl, dimethylaminoethyl, diethylaminoethyl, phenyl, xylyl, naphthyl, pentachlorophenyl, trichlorophenyl, p-methanesulfonylphenyl, p-phenylazophenyl, dinitrophenyl, pyridyl, quinolyl, benzyl, phenethyl, nitrobenzyl, chlorobenzyl, trimethoxybenzyl, benzhydryl, p,p'-dimethoxydiphenylmethyl, pentachlorobenzyl, 4-oxy-3,5-ditertiary butylbenzyl, pyridylmethyl, quinolylmethyl, and vinyl;

the broken line shows a double bond at position 2 or 3; and n is zero or one.

2. A compound claimed in claim 1 wherein R$^1$ is an alkyl containing 1 to 8 carbon atoms or phenyl.

3. A compound claimed in claim 1 wherein R$^2$ is lithium or a half mole of magnesium.

4. A compound claimed in claim 1 wherein R$^2$ is a halomagnesio group.

5. A compound claimed in claim 1 wherein $R^3$ is a hydrogen, sodium, diphenylmethyl, or p-nitrobenzyl.

6. A compound claimed in claim 1 wherein Acyl is a 2-thienylacetyl or phenoxyacetyl.

7. A compound claimed in claim 1 wherein $n$ is zero.

8. A compound claimed in claim 1 wherein $n$ is one and S↭O bond represents α or β configuration.

9. A compound claimed in claim 1 wherein the broken line represents the presence of a double bond at position 2.

10. A compound claimed in claim 1 wherein the broken line represents the presence or a double bond at position 3.

11. A compound selected from the following compounds:

methyl 7β-(2-thienylacetamido)-3-(1-iodomagnesiooxyethyl)-2-cephem-4-carboxylate,
diphenylmethyl 7β-(2-thienylacetamido)-3-(1-iodomagnesiooxyethyl)-2-cephem-4-carboxylate,
diphenylmethyl 7β-(2-thienylacetamido)-3-(1-iodomagnesiooxyethyl)-3-cephem-4-carboxylate,
diphenylmethyl 7β-(2-thienylacetamido)-3-(1-iodomagnesiooxyethyl)-3-cephem-4-carboxylate 1-oxide,
diphenylmethyl 7β-(2-thienylacetamido)-3-(1-lithiooxyethyl)-2-cephem-4-carboxylate,
diphenylmethyl 7β-(2-thienylacetamido)-3-(α-bromomagnesiooxybenzyl)-2-cephem-4-carboxylate,
diphenylmethyl 7β-(2-thienylacetamido)-3-(α-bromomagnesiooxybenzyl)-3-cephem-4-carboxylate,
p-nitrobenzyl 7β-phenoxyacetamido-3-(1-bromomagnesiooxyethyl)-2-cephem-4-carboxylate, and
p-nitrobenzyl 7β-phenoxyacetamido-3-(1-magnesiooxybutyl)-3-cephem-4-carboxylate.

* * * * *